(12) United States Patent
Sakaguchi et al.

(10) Patent No.: US 7,214,849 B2
(45) Date of Patent: May 8, 2007

(54) DISPOSABLE WEARING ARTICLE

(75) Inventors: Saturo Sakaguchi, Mitoyo-gun (JP); Hiroki Ishikawa, Mitoyo-gun (JP); Satoshi Mitsuno, Mitoyo-gun (JP)

(73) Assignee: Uni-Charm Corporation, Ehime-ken (JP)

( * ) Notice: Subject to any disclaimer, the term of this patent is extended or adjusted under 35 U.S.C. 154(b) by 282 days.

(21) Appl. No.: 11/074,639

(22) Filed: Mar. 9, 2005

(65) Prior Publication Data
US 2005/0203472 A1 Sep. 15, 2005

(30) Foreign Application Priority Data
Mar. 12, 2004 (JP) .............................. 2004-070344

(51) Int. Cl.
*A61F 13/15* (2006.01)
(52) U.S. Cl. ...................... 604/361; 604/365; 604/366; 604/367; 604/385.01
(58) Field of Classification Search ................ 604/361, 604/385.01, 365, 366, 367
See application file for complete search history.

(56) References Cited

U.S. PATENT DOCUMENTS 5,690,624 A * 11/1997 Sasaki et al. ............... 604/361
6,506,698 B1 * 1/2003 Quantrille et al. .......... 442/361

FOREIGN PATENT DOCUMENTS

JP 2002-657 1/2002

* cited by examiner

*Primary Examiner*—Jacqueline F. Stephens
(74) *Attorney, Agent, or Firm*—Lowe Hauptman & Berner LLP

(57) ABSTRACT

A wearing article is provided on at least one of front and rear waist covering regions with an indication element adapted to be visually recognized from the outside of the article. The waist covering region provided with the indication element includes a first composite sheet, a second composite sheet lying inside this first composite sheet and the indication element interposed between these two composite sheets. The first composite sheet comprises a first intermediate layer, a first outer layer and a first inner layer while the second composite sheet includes a second intermediate layer, a second outer layer and a second inner layer. The respective layers of the first composite sheet are joined together at joining spots arranged intermittently in a waist-surrounding direction. The first outer layer, the first inner layer, the second outer layer and the second inner layer are respectively formed from inelastic threads describing curves which are stretchable in the waist-surrounding direction between each pair of adjacent joining spots.

3 Claims, 5 Drawing Sheets

DISPOSABLE WEARING ARTICLE

RELATED APPLICATIONS

The present application is based on, and claims priority from, Japanese Application Ser. No. 2004-70344, filed Mar. 12, 2004, the disclosure of which is hereby incorporated by reference herein in its entirety.

BACKGROUND OF THE INVENTION

The present invention relates to a disposable wearing article and more particularly to a disposable wearing article including an indication element adapted to be visually recognized from the outside of the wearing article.

In disposable wearing articles such as disposable diapers or disposable training pants, it is well known to provide a front waist covering region and/or a rear waist covering region with indication element(s) adapted to be visually recognized from the outside of the wearing article. In the case of an absorbent article disclosed in Japanese Unexamined Patent Application Publication No. 2002-657 (hereinafter referred to as "Citation"), a backsheet comprises a film printed with an illustration and a nonwoven fabric laminated on the surface of this film which is printed with the illustration adapted to be visually recognized through the nonwoven fabric.

Citation contains a description such that a luminous transmissivity of the nonwoven fabric laminated on the film must be enhanced in order to ensure a desired visibility of the illustration. Citation further contains a description such that the nonwoven fabric laminated on the film preferably has a basis weight in a range of 20 to 50 $g/m^2$ and a thickness in a range of 0.5 to 3 mm on account of a fact that the basis weight of the nonwoven fabric may be decreased to enhance the luminous transmissivity of the nonwoven fabric but texture and touch are deteriorated as the basis weight of the nonwoven fabric is decreased. In this manner, an upper limit is imposed on the basis weight of the nonwoven fabric constituting the backsheet of such absorbent article as disclosed in Citation and quality or visibility of the illustration is deteriorated as the basis weight of the nonwoven fabric gets near to or exceeds the upper limit imposed thereon.

SUMMARY OF THE INVENTION

It is an object of the present invention to provide the disposable wearing article including the indication element such as the illustration which is covered with a sheet-like fibrous aggregate in the visually recognizable manner improved so that a flexible touch of the article around the indication element can be enhanced without sacrificing the visibility of the indication element.

According to the present invention, there is provided a disposable wearing article having a front waist covering region, a rear waist covering region and a crotch covering region cooperating together to form the wearing article with a waist-hole and a pair of leg-holes wherein at least one of the front and rear waist covering regions is elastically stretchable in a waist-surrounding direction and provided with an indication element adapted to be visually recognized from an outside of the at least one waist covering region.

The wearing article further comprises the indicating element including a sheet strip; the at least one covering region comprising a first composite sheet and a second composite sheet, the first composite sheet lying on an outermost side of the at least one covering region and having a first outer surface defining an outer surface of the at least one covering composite sheet and a first inner surface lying on a side opposite to the first outer surface while the second composite sheet lying on the side of the first inner surface of the first composite sheet and having a second outer surface facing the second inner surface and having a second outer surface and a second inner surface lying on the side opposite to the second outer surface with the sheet strip being interposed between the first inner surface and the second outer surface; and the first and second composite sheets are respectively of three-layered structure being bonded together at bonding spots formed intermittently in the waist-surrounding direction and respectively comprising first and second intermediate layers formed by a plurality of elastically stretchable elastomer threads accumulated one upon another, first and second outer layers formed by a plurality of inelastically stretchable non-elastomeric threads accumulated one upon another and stretchably extending in the waist-surrounding direction so as to describe curves between each pair of the adjacent bonding spots on the outer sides of the first and second intermediate layers, respectively, and first and second inner layers formed by a plurality of inelastically stretchable non-elastomeric threads accumulated one upon another and stretchably extending in the waist-surrounding direction so as to describe curves between each pair of the adjacent bonding spots on the inner sides of the first and second intermediate layers, respectively, wherein the first and second outer layers define the first and second surfaces, respectively.

In such disposable wearing article according to the invention, at least one of the front and rear waist covering regions comprises the first composite sheet and the second composite sheet wherein the indication element is interposed between the first inner layer of the first composite sheet and the second outer layer of the second composite sheet and the first composite sheet allows the indication element to be visually recognized from the outside of the article. The elastic threads making the waist covering regions elastically stretchable in the waist-surrounding direction of the wearing article are present in the first and second intermediate layers of the first and second composite sheets, respectively, and the inelastic threads are present in the first outer layer and the first inner layer of the first composite sheet and the second outer layer and the second inner layer of the second composite sheet. The basis weight of the second intermediate layer may be increased to enhance the elastic stretch stress of the waist covering regions and the basis weight of the second outer layer as well as the second inner layer may be increased to enhance the flexible touch of the waist covering regions. The present invention allows the basis weight of the second intermediate layer and/or the second outer layer and/or the second inner layer to be increased without sacrificing the visibility of the indication element.

According to one preferred embodiment of the invention, the first outer layer, the first intermediate layer and the first inner layer of the first composite sheet have a basis weight in a range of 5 to 25 $g/m^2$, respectively, while the second outer layer, the second intermediate layer and the second inner layer of the second composite sheet have a basis weight of at least 5 $g/m^2$, respectively.

In the wearing article according to this embodiment, the amount of the inelastic threads may be distributed larger in the first outer layer than in the first inner layer to improve the flexible touch provided by the outer surface of the waist covering regions so far as the amount of the inelastic threads used in the first composite sheet is constant.

According to another preferred embodiment of the invention, outside a periphery of the sheet strip, the inelastic threads of the first inner layer and the inelastic threads of the second outer layer are intertangled together.

In the wearing article according to this embodiment, the inelastic threads of the first inner layer and the inelastic threads of the second outer layer are intertangled together and thereby the first and second composite sheets are reliably integrated together without relying on use of adhesive or welding technique. In this way, it is not apprehended that the touch of the waist covering regions might be uncomfortably stiffened due to use of adhesive or welding technique.

DETAILED DESCRIPTION OF THE PREFERRED EMBODIMENTS

Details of a disposable wearing article will be more fully understood from the description given hereunder with reference to the accompanying drawings.

Figure 1:
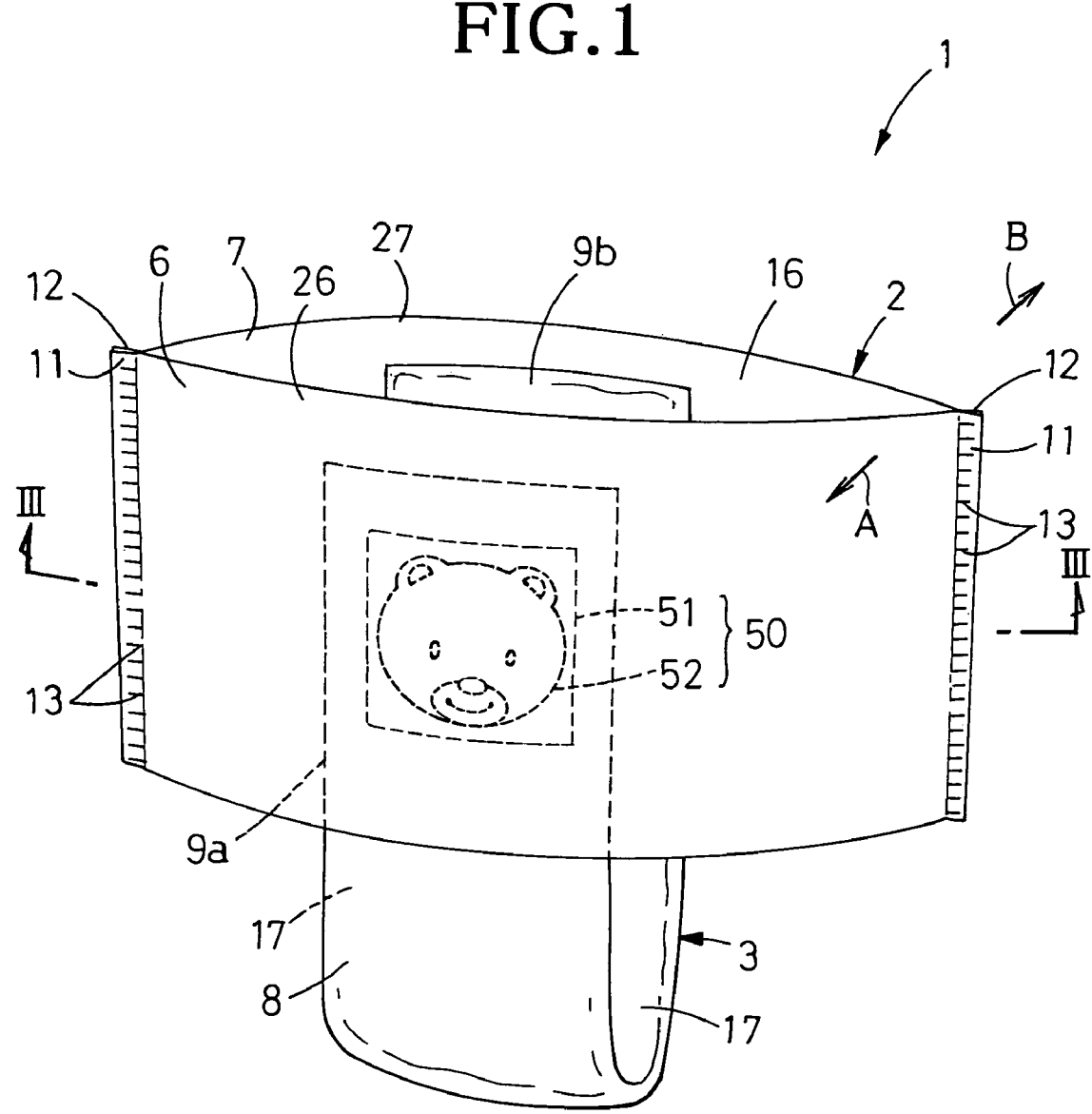
FIG. 1 is a perspective view showing a disposable diaper as an example of a disposable wearing article.

A pants-type (or pull-on type) disposable diaper 1 shown in FIG. 1 in a perspective view is as one embodiment of a disposable wearing article has a waist covering member 2 formed to be annular and a crotch covering member 3 formed in a U-shape. The waist covering member 2 comprises a front waist covering region 6 and a rear waist covering region 7 wherein these two covering regions 6, 7 respectively have transversely opposite marginal portions 11, 12 along which these two waist covering regions 6, 7 are overlapped and joined together at joining spots 13 arranged intermittently in a vertical direction as viewed in FIG. 1. The crotch covering member 3 comprises a crotch covering region 8 and front and rear joining regions 9a, 9b (See FIG. 2 also) lying above the crotch covering region 8. These joining regions 9a, 9b are joined to an inner surface of the front waist covering region 6 and to an inner surface of the rear waist covering region 7, respectively, by means of adhesives 37 (See FIG. 3). In such diaper 1, the front waist covering region 6 cooperates with the rear waist covering region 7 to form a waist-hole 16 while these waist covering regions 6, 7 cooperate with the crotch covering region 8 to form a pair of leg-holes 17. An illustration 52 of a bear's head printed on a sheet strip 51 is visible from the outside of the front waist covering region 6.

Figure 2:
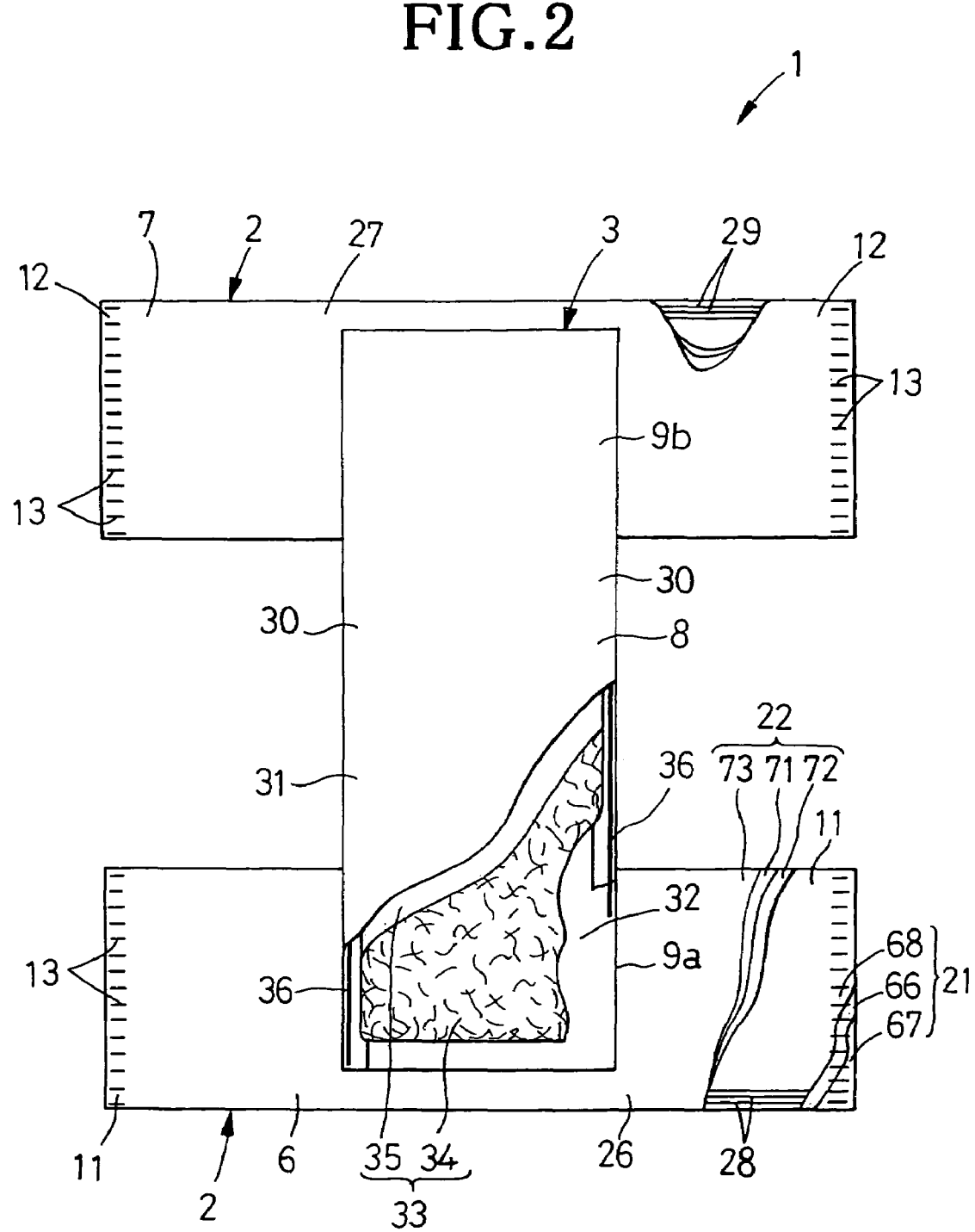
FIG. 2 is a partially cutaway plan view of the disposable diaper developed in a back-and-forth direction.

FIG. 2 is a partially cutaway developed plan view showing the diaper 1 with the front and rear waist covering regions 6, 7 having been peeled off from each other along the transversely opposite lateral portions 11, 12 at the joining spots 13 and developed forward as indicated by an arrow A and rearward as indicated by an arrow B.

The front and rear waist covering regions 6, 7 constituting the waist covering member 2 shown in FIG. 2 respectively comprise an outer composite sheet 21 facing an undergarment and an inner composite sheet 22 facing the wearer's body when the diaper 1 is put on the wearer. These outer composite sheet 21 and inner composite sheet 22 are elastically stretchable in at least one of a waist-surrounding direction of the waist covering member 2 and a vertical direction orthogonal to this waist-surrounding direction. These composite sheets 21, 22 will be described in reference with FIG. 5.

The crotch covering member 3 shown in FIG. 2 has a substantially rectangular shape and comprises a liquid-pervious topsheet 31, a liquid-impervious backsheet 32 and a liquid-absorbent core 33 interposed between these sheets 31, 32. Portions of the top- and backsheets 31, 32 extending outward beyond a peripheral edge of the core 33 are joined to each other by means of adhesives (not shown). Along transversely opposite marginal portions 34 of the crotch covering member 3 outside the core 33, leg-surrounding elastic members 36 extend in the vertical direction as viewed in FIG. 2 and joined in a stretched state to the inner surface (See FIG. 3) of the topsheet 31 by means of adhesives (not shown).

Figure 3:
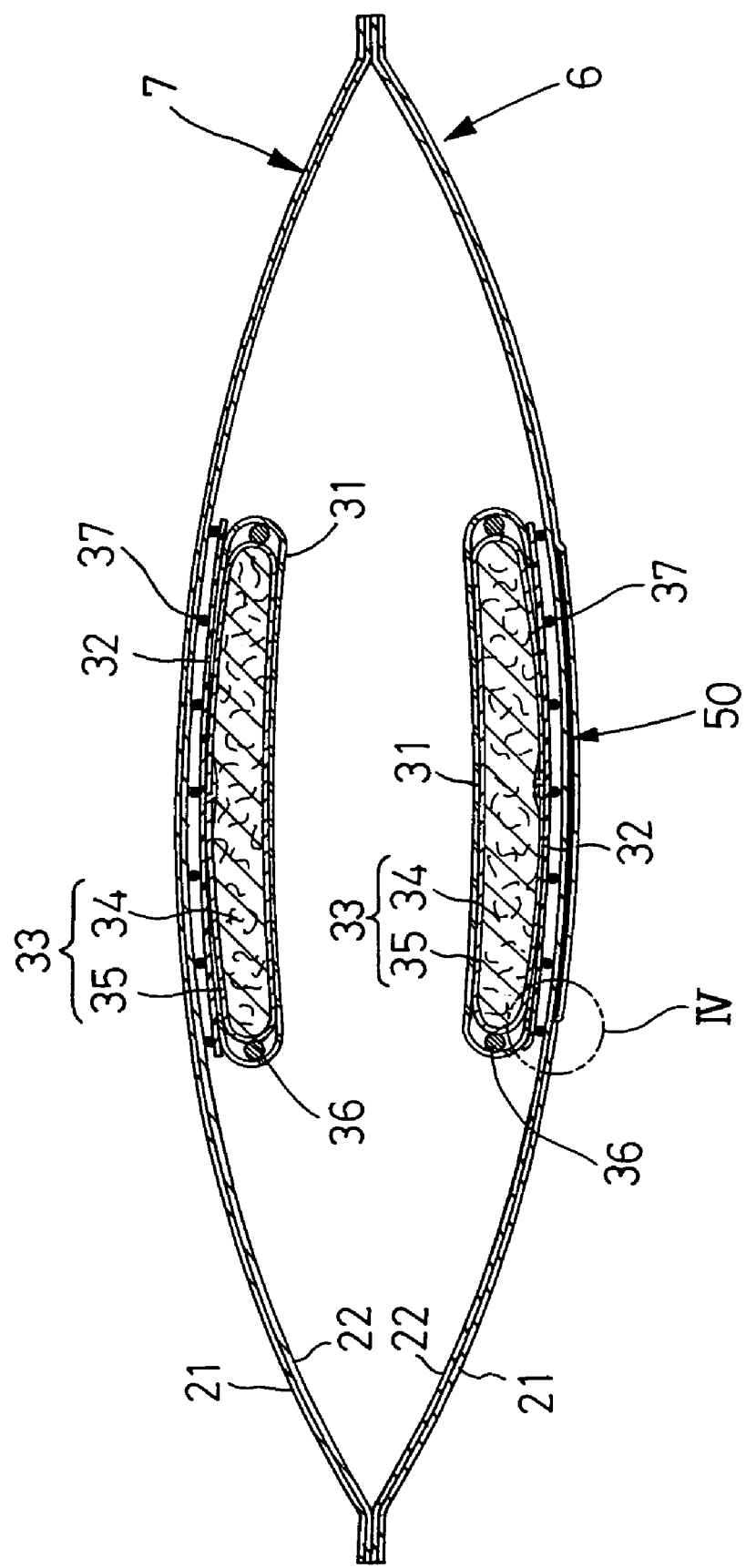
FIG. 3 is a sectional view taken along the line III—III in FIG. 1.

FIG. 3 is a sectional view taken along the line III—III in FIG. 1. The crotch covering member 3 lies inside the waist covering member 2 formed in an annular shape and the backsheet 32 constituting the crotch region 3 has front and rear joining areas 9a, 9b in which the backsheet 32 is joined to the inner composite sheet 22 in the front and rear waist covering regions 6, 7 by means of adhesives 37. The core 33 contained in the crotch covering member 3 comprises a liquid-absorbent material 34 such as fluff pulp and/or super-absorbent polymer particles and highly liquid-diffusible and liquid-pervious sheet such as a tissue paper 35 wrapping the material 34. Leg-surrounding elastic members 36 are secured to the inner surface of the topsheet 31 constituting the crotch covering member 3. In a transversely middle zone of the front waist covering region 6, an indicator means 50 is interposed between the outer composite sheet 21 and the inner composite sheet 22. As will be described in more detail with reference to FIG. 4, the indicator means 50 comprises a sheet strip 51 such as a plastic film, paper, nonwoven fabric and woven fabric and an indication element 52 formed by printing an illustration of bear's head on the sheet strip 51. The sheet strip 51 is joined to the outer composite sheet 21 and/or the inner composite sheet 22 using suitable adhesives or welding technique with the indication element 52 facing the outer composite sheet 21.

Figure 4:
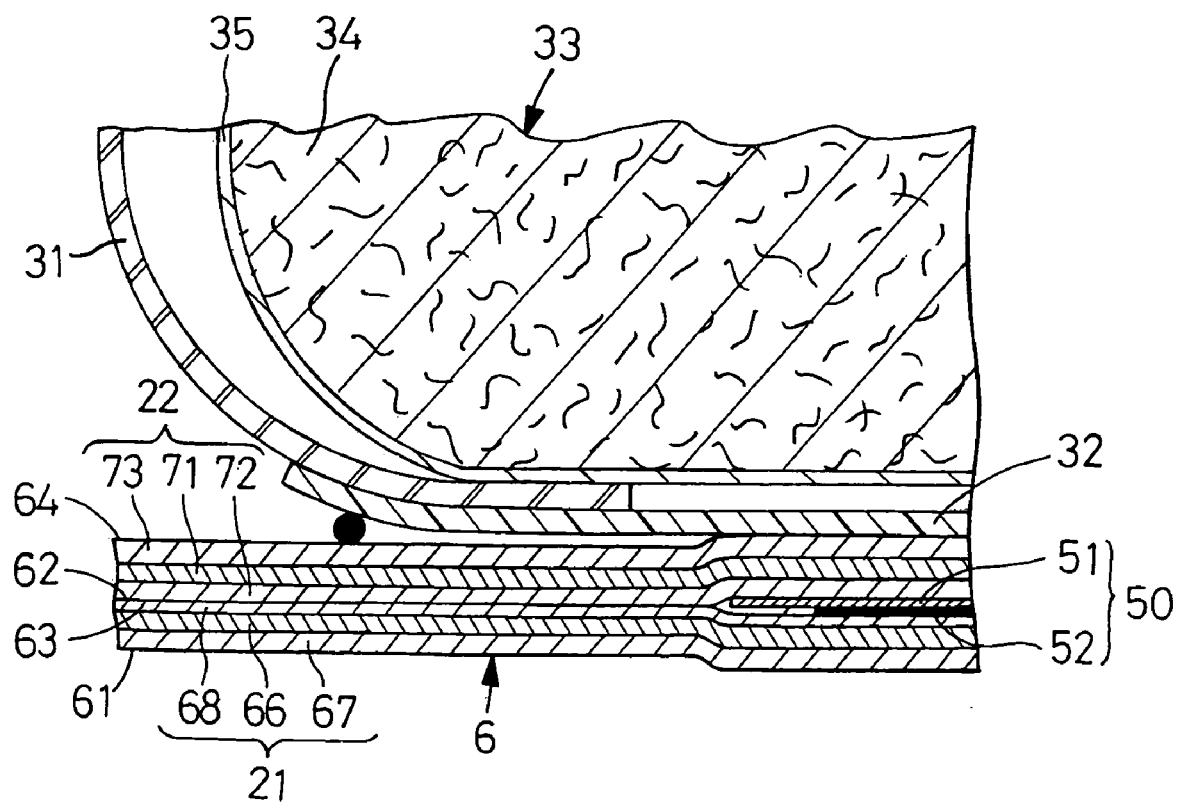
FIG. 4 is a view showing a part of FIG. 3 in an enlarged scale.

FIG. 4 is a view showing a part of FIG. 3 encircled by a chain line IV. In the front waist covering region 6, the outer composite sheet has a first outer surface 61 defining the outer surface of the front waist covering region 6 and a second inner surface 62 defining a surface opposed to the first outer surface 61. The inner composite sheet 22 has a second outer surface 63 facing the first inner surface 62 and a second inner surface 64 opposed to the second outer surface 63 so as to define the inner surface of the front waist covering region 6. Both the outer composite sheet 21 and the inner composite sheet 22 are of a trilaminar structure. Specifically, the outer composite sheet 21 comprises a first intermediate layer 66, a first outer layer 67 lying outside the first intermediate layer 66 so as to define the first outer surface 61 and a first inner layer 68 lying inside the first intermediate layer 66 so as to define the first inner surface 62 wherein these first outer layer 67, first intermediate layer 66 and first inner layer 68 are placed one upon another in this order as shown and joined one to another intermittently in the waist-surrounding direction using suitable adhesives or welding technique. The inner composite sheet 22 comprises a second intermediate layer 71, a second outer layer 72 lying outside the second intermediate layer 71 so as to define the second outer surface 63 and a second inner layer 73 lying inside the second intermediate layer 71 so as to define the second inner surface 64 wherein these second outer layer 72, second intermediate layer 71 and second inner layer 73 are placed one upon another in this order as shown and joined one to another intermittently in the waist-surrounding direction using suitable adhesives or welding technique.

Of the outer composite sheet 21, the first intermediate layer 66 comprises a plurality of elastic threads made from elastomer accumulated one upon another and fused or intertangled together. The preferred first intermediate layer 66 comprises aggregate of the elastic threads made of continuous fibers (filaments) having a fineness in a range of 0.1 to 5 dtx and a basis weight in a range of 5 to 25 g/m². Such first intermediate layer 66 is elastically stretchable in at least one of the waist-surrounding direction of the waist covering member 2 and the vertical direction orthogonal to the waist-surrounding direction. An elastic stretchability of this first intermediate layer 66 is adjusted so that an elastic recovery R of the outer composite sheet 21 in the waist-surrounding direction may be 80% or higher. Using a test piece having a width of 10 mm and a length of 70 mm cut away from the outer composite sheet 21, the elastic recovery R is obtained from an equation as follows:

$$R(\%) = \frac{L_1 - L_2}{L_1 - L_0} \times 100$$

wherein $L_0$ represents a dimension between a pair of chucks clamping longitudinally opposite end portions of the test piece over a length of 10 mm, respectively, $L_1$ represents a dimension between the chucks after $L_0$ has been stretched by 50% and $L_2$ represents a dimension between the chucks as measured 10 seconds after the test piece was held at the dimension $L_1$ for 2 seconds and then has been left to contract.

Both the first outer layer 67 and the first inner layer 68 constituting the outer composite sheet 21 are formed from a plurality of inelastic threads exhibiting no behavior as elastomer which are accumulated one upon another. The preferred first outer layer 67 and the first inner layer 68 respectively comprise aggregates of inelastic threads made of continuous fibers (filaments) having a fineness in a range of 0.05 to 5 dtx and a basis weight of 5 to 25 g/m². The basis weight of the preferred first outer layer 67 may be same as or higher than the basis weight of the first inner layer 68.

Figure 5:
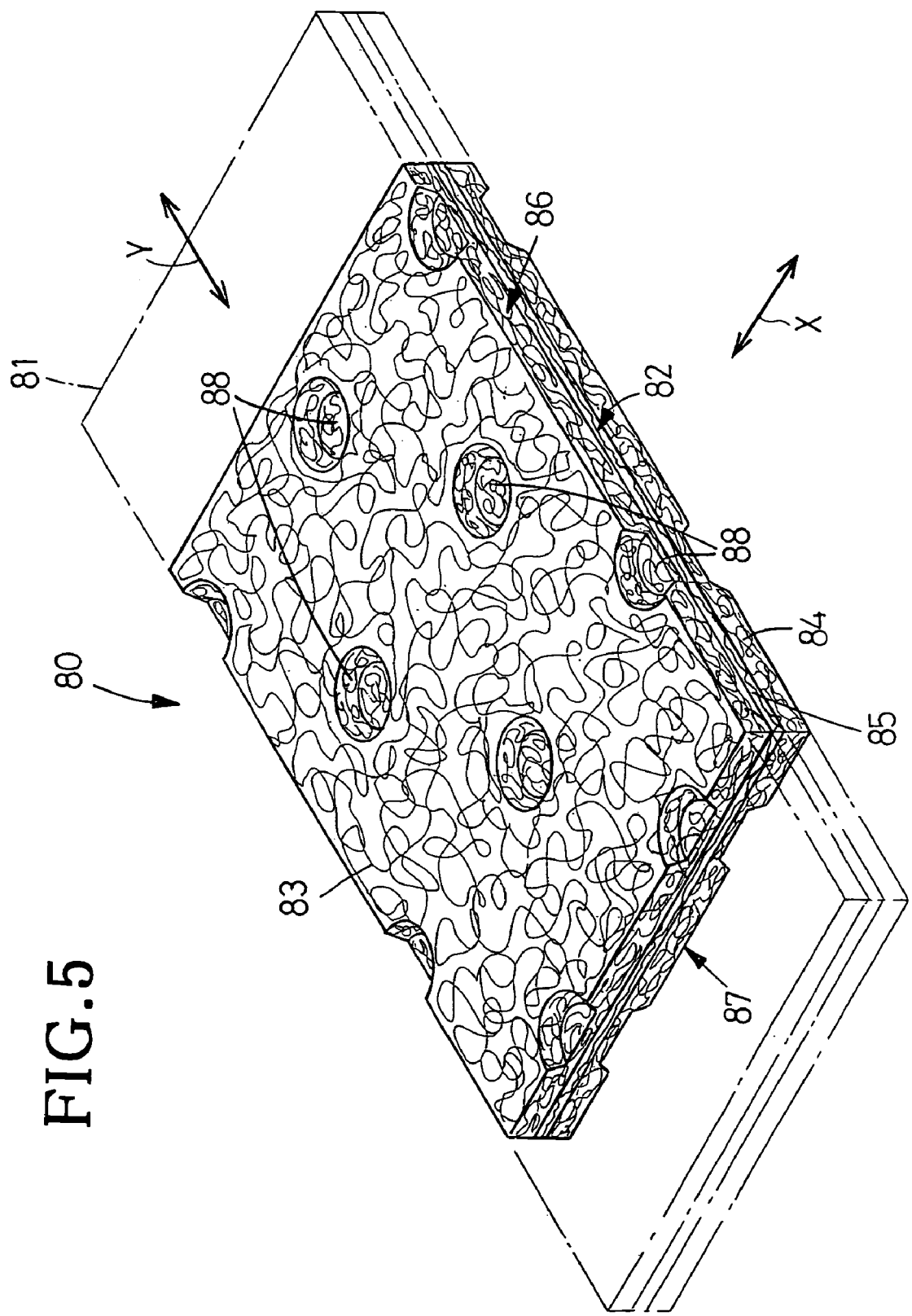
FIG. 5 is a diagram illustrating an example of the composite sheet.

FIG. 5 is a perspective view exemplarily showing a composite sheet 80 practically useful as the outer composite sheet 21. This composite sheet 80 is obtained on the basis of Japanese Unexamined Patent Application Publication No. 2001-79972 filed by the present applicant and comprises an elastically stretchable intermediate layer sheet 82 formed from elastic threads 85 made from a plurality of elastically stretchable continuous fibers (filaments), and upper and lower layer sheets 86, 87 respectively joined by aggregates of inelastic threads 83, 84 made from a plurality of inelastically stretchable continuous fibers (filaments) wherein these upper and lower layer sheets 86, 87 are joined to upper and lower surfaces of the intermediate layer sheet 82, respectively, at a plurality of joined spots 88 formed intermittently in a direction indicated by a double-headed arrow X and a direction indicated by a double headed arrow Y orthogonal to the direction of the double-headed arrow X. Each of the inelastic threads 83 is continuous between each pair of the adjacent joined spots 88 containing this inelastic thread 83 therein and each of the inelastic threads 84 also is continuous between each pair of the adjacent bonding spots 88 containing this inelastic thread therein. The inelastic threads 83 as well as the inelastic threads 84 are respectively separated one from another and describe irregular curves between each pair of the adjacent joining spots 88 containing these inelastic threads 83, 84. Assumed, for example, that the composite sheet 80 is stretched in the direction of the double-headed arrow Y until the composite sheet 80 becomes a composite sheet 81 indicated by an imaginary line, the intermediate layer sheet 82 is elastically stretched and, in response to this, the inelastic threads 83, 84 describing curves in the upper and lower sheets 86, 87, respectively, are progressively reoriented between each pair of the adjacent joining spots 88 containing both of the inelastic threads 83, 84 until these inelastic threads 83, 84 linearly extend in the direction of the double-headed arrow Y. In the stretched composite sheet 81, the intermediate layer sheet 82 is elastically contractible to restore the composite sheet 80 indicated by a solid line and, in response to this, the inelastic threads 83, 84 once having been substantially straightened restore the initial curves thereof. At the joining spots 88, the upper layer sheet 86, the intermediate layer sheet 82 and the lower layer sheet 87 are integrated together using suitable welding technique or adhesives, preferably using suitable welding technique. The elastic threads 85 may be made from thermoplastic elastomer fibers. Materials for the inelastic threads 83, 84 may be selected from the group including polypropylene, ethylene-propylene random copolymer, ethylene-propylene-butene random copolymer, polyester and polyethylene.

On the assumption that such composite sheet 80 is used as the outer composite sheet 21, the direction of the double-headed arrow Y corresponds to the waist-surrounding direction, the intermediate layer sheet 82 corresponds to the first intermediate layer 66, the upper layer sheet 86 corresponds to the first outer layer 67 and the lower layer sheet 87 corresponds to the first inner layer 68. The elastic threads 85 correspond to the elastic threads constituting the first intermediate layer 66 and the inelastic threads 83, 84 correspond to the inelastic threads constituting the first outer layer 67 and the first inner layer 68, respectively. The outer composite sheet 21 comprises a plurality of joining spots similar to the joining spots 88 exemplarily illustrated in FIG. 5. Between each pair of the adjacent joining spots, the inelastic threads constituting the first outer layer 67 as well as the inelastic threads constituting the first inner layer 68 extend in the circumferential direction of the front waist covering region 6 and the vertical direction of the front waist covering region 6 orthogonal to the circumferential direction so as to describe irregular curves. The first outer layer 67 and the first inner layer 68 are joined to the first intermediate layer 66 at the respective joining spots so that, as the first intermediate layer 66 is elastically stretched in the circumferential direction and/or in the direction orthogonal to the circumferential direction, the inelastic threads having described the irregular curves in the first outer layer 67 and the first inner layer 68 until that moment are stretched in the same directions as those in which the first intermediate layer 66 is stretched and are progressively deformed so as to be substantially straightened. Elastic contraction of the first intermediate layer 66 causes, on the contrary, the inelastic threads having been substantially straightened in the first outer layer 67 as well as in the first inner layer 68 until that moment to describe again the initial irregular curves. During deformation of the inelastic threads constituting the first outer layer 67 and the first inner layer 68 from the irregularly curved states to the substantially straightened states, the first intermediate layer 66 can be elastically stretched and contracted without any significant affection by such deformation of the inelastic threads. Therefore, in spite of the fact that the outer composite sheet 21 is of a three-layered structure, the elastic threads constituting the first intermediate layer 66 can exhibit the stretch/contraction characteristics peculiar to these elastic threads.

In the inner composite sheet 22, the second intermediate layer 71 is formed from the elastic threads accumulated one upon another and fused or intertangled together. The preferred second intermediate layer 72 comprises an aggregate of continuous fibers (filaments) having a fineness in a range of 0.1 to 8 dtx and a basis weight of 5 $g/m^2$, more preferably in a range of 5 to 50 $g/m^2$. This second intermediate layer 71 is elastically stretchable in at least one of the circumferential direction of the waist covering member 2 and the vertical direction orthogonal to this circumferential direction. This elastic stretchability of the second intermediate layer 71 is adjusted so that the elastic recovery R of the inner composite sheet 22 in the waist-surrounding direction may be 80% or higher. The elastic recovery R is the value obtained by the same measuring method as used for the first intermediate layer 66 of the outer composite sheet 21.

The second outer layer 72 as well as the second inner layer 73 constituting the inner composite sheet 22 are formed from a plurality of inelastic threads accumulated one upon another similarly to the case of the first outer layer 67 as well as the first inner layer 68. The preferred second outer layer 72 and second inner layer 73 comprise aggregates each made of the inelastic threads having a fineness in a range of 0.05 to 5 dtx and a basis weight of 5 $g/m^2$ or higher, more preferably in a range of 5 to 50 $g/m^2$.

The composite sheet 80 exemplarily illustrated in FIG. 5 is also useful as the inner composite sheet 22. Assumed that the composite sheet 80 is used as the inner composite sheet 22, the intermediate layer sheet 82 corresponds to the second intermediate layer 71, the upper layer sheet 86 corresponds to the second outer layer 72 and the lower layer sheet 87 corresponds to the second inner layer 73. The elastic threads 85 constitute the second intermediate layer 71 and the inelastic threads 83, 84 constitute the second outer layer 72 and the second inner layer 73, respectively. The inner composite sheet 22 comprises a plurality of joining spots as exemplarily illustrated in FIG. 5 as the joining spots 88. Between each pair of the adjacent joining spots, the inelastic threads constituting the second outer layer 72 as well as the inelastic threads constituting the second inner layer 73 extend in the circumferential direction of the front waist covering region 6 and the vertical direction of the front waist covering region 6 orthogonal to the circumferential direction so as to describe irregular curves. The second outer layer 72 and the second inner layer 73 are joined to the second intermediate layer 71 at the respective joining spots so that, as the second intermediate layer 71 is elastically stretched in the circumferential direction and/or in the vertical direction orthogonal to the circumferential direction, the inelastic threads having described the irregular curves in the second outer layer 72 and the second inner layer 73 until that moment are stretched in the same directions as those in which the second intermediate layer 71 is stretched and are progressively deformed so as to be substantially straightened. Elastic contraction of the second intermediate layer 71 causes, on the contrary, the inelastic threads having been substantially straightened in the second outer layer 72 as well as in the second inner layer 73 until that moment are deformed again to describe the initial irregular curves. During deformation of the inelastic threads constituting the second outer layer 72 and the second inner layer 73 from the irregularly curved states to the substantially straightened states, the second intermediate layer 71 can be elastically stretched and contracted without any significant affection by such deformation of the inelastic threads. Therefore, the elastic threads constituting the second intermediate layer 71 can exhibit the stretch/contraction characteristics peculiar to these elastic threads.

The sheet strip 51 constituting the indicator means 50 in FIG. 4 is interposed between the first inner layer 68 and the second outer layer 72 constituting the outer composite sheet 21 and joined to at least one of these two layers 68, 72 using suitable adhesives or welding technique. For the indication element 52 in the form of an illustration serving as the other component of the indicator means 50, printing ink of an appropriate color tone is used, which facilitates the indication element 52 to be visually recognized through the outer composite sheet 21.

In the front waist covering region 6 constructed in this manner, the outer composite sheet 21 preferably has a luminous transmissivity of 60% or higher in order that the indication element 52 is distinctly visible through the outer composite sheet 21. To achieve the luminous transmissivity of such level, the outer composite sheet 21 preferably has a basis weight of 50 $g/m^2$ or less. While staple fibers (staple fibers) may be used as materials for the elastic threads and the inelastic threads in the outer composite sheet 21, the outer composite sheet 21 using such short fibers will be apt to be excessively nap-raised due to the presence of many fiber ends. The excessively nap-raised outer composite sheet 21 may often blur the indication element 52 which should be visible through the outer composite sheet 21 as vividly as possible. Such a problem can be solved by using the continuous fibers (filaments) as material for the elastic threads and the inelastic fibers. Both the first outer layer 67 and the first inner layer 68 in the outer composite sheet 21 are preferably made of materials which can provide the outer composite sheet with a cloth-like touch. To achieve this, the basis weight of the first outer layer is preferably the same as or higher than the basis weight of the first inn layer 68 on the assumption that a sum of the basis weight of the first outer layer 67 and the basis weight of the first inner layer 68 is constant. In this way, it is ensured that the diaper wearer experiences no rubber-like touch peculiar to the first intermediate layer 66 but rather cloth-like soft touch even when the diaper wearer's skin comes in contact with the outer composite sheet 22. In the inner composite sheet 22, the second intermediate layer 71 cooperates with the first intermediate layer 66 to provide the front waist covering region 6 with the elastic stretchability in the waist-surrounding direction and the vertical direction, more strictly, at least in the waist-surrounding direction. In a zone extending outside the periphery of the sheet strip 51, the second outer layer 72 is held in contact with the first inner layer 68 and, along the interface between these two layers 68, 72, the inelastic threads extending so as to describe the irregular curves are intertangled together so that these two layers 68, 72 may be substantially integrated with each other. These two layers 68, 72 integrated with each other in this manner can be integrally stretched in the waist-surrounding direction and in the vertical direction. These two layers 68, 72 are integrated with each other not by means of adhesives or welding technique and therefore it is not apprehended that the layers 68, 72 might be stiffened and give the diaper wearer uncomfortable touch due to use of adhesives or welding technique.

In addition, there is no anxiety that these two layers 68, 72 might move from each other and deteriorate a desired fitness to the wearer's body. The second inner layer 73 covers the second intermediate layer 71 comprising the elastic threads and thereby prevents the rubber-like touch peculiar to the second intermediate layer 71 from being transmitted to the inner surface of the front waist covering region 6 so that the inner surface of the front waist covering region 6 may present the cloth-like touch. If it is desired to enhance the elastic stretch stress of the front waist covering region 6 in the waist-surrounding direction, it is preferred to enhance the basis weight of the second intermediate layer 71 correspondingly. If it is desired to improve the flexibility of the front waist covering region 6, it is preferred to enhance the basis weight of the second outer layer 72 as well as the second inner layer 73. In this way, it is not apprehended that the visibility of the indication element 52 might be deteriorated even if the basis weight is enhanced.

The present invention may be exploited whether the rear waist covering region 7 is provided with the indicator means 50 or not. The rear waist covering region 7 provided with the indicator means 50 may be constructed in the same manner as the illustrated front waist covering region 6. The rear waist covering region 7 provided with no indicator means 50 may be formed by one or more layers of elastically stretchable nonwoven fabric or film or inelastic nonwoven fabric or film.

The present invention may be exploited also in the manner that the front waist covering region 6 is provided with no indicator means 50 and the rear waist covering region 7 is provided with the indicator means 50. The front waist covering region 6 provided with no indicator means 50 may be formed from a nonwoven fabric or film having no elastic stretchability in the waist-surrounding direction. While the indication element 52 is illustrated to be formed from the sheet strip 51 partially printed, such indication element 52 may be replaced by an appropriately shaped sheet strip such as a strip of film, paper or the like which is directly colored or printed.

The present invention may be exploited also in the manner that the annular waist covering member 2 of the illustrated diaper 1 is replaced by a pants-type waist covering member comprising, in addition to the front waist covering region 6 and the rear waist covering region 7, a crotch covering region. In this case, it is possible to attach the illustrated crotch covering member 3 to the inner surface of such waist covering member. When such waist covering member is adopted, it is also possible to use a liquid-impervious plastic film as a material for the sheet strip 51 constituting the indicator means 50 in cooperation with the indication element 52 and to form the indicator means 50 which continuously extend from the front waist covering region 6 to the rear waist covering region 7 through the crotch covering region. In the case of the diaper 1 having such sheet strip 51, it is possible to prevent body fluids can be from leaking beyond the crotch covering member 3 out of the diaper 1 even when the liquid-impervious backsheet 32 exemplarily shown in FIGS. 2, 3 and 4 is formed, for example, using a liquid-pervious sheet such as the liquid-pervious topsheet 31.

While the present invention has been described above on the basis of the disposable diaper as one embodiment, the invention is applicable to the wearing article such as disposable training pants and disposable diapers for incontinent patient.

The present invention is effectively applicable to produce the disposable diaper of which the elastically stretchable waist covering region presents a flexible touch and including the visible indicating elements.

What is claimed is:

1. A disposable wearing article comprising:
   a front waist covering region; a rear waist covering region and a crotch covering region cooperating together to form the wearing article with a waist-hole and a pair of leg-holes wherein at least one of said front and rear waist covering regions is elastically stretchable in a waist-surrounding direction and provided with an indication element adapted to be visually recognized from an outside of said at least one waist covering region;
   said indicating element including a sheet strip;
   said at least one covering region comprising a first composite sheet and a second composite sheet, said first composite sheet lying on an outermost side of said at least one covering region and having a first outer surface defining an outer surface of said one covering composite sheet and a first inner surface lying on a side opposite to said first outer surface while said second composite sheet lying on a side of said first inner surface of said first composite sheet and having a second outer surface facing said second inner surface and having a second outer surface and a second inner surface lying on a side opposite to said second outer surface with said sheet strip being interposed between said first inner surface and said second outer surface; and
   said first and second composite sheets being respectively of a three-layered structure joined together at joining spots formed intermittently in said waist-surrounding direction and respectively comprising first and second intermediate layers formed from a plurality of elastically stretchable elastomer threads accumulated one upon another, first and second outer layers formed from a plurality of inelastically stretchable non-elastomeric threads accumulated one upon another and stretchably extending in said waist-surrounding direction so as to describe curves between each pair of adjacent joining spots on outer sides of said first and second intermediate layers, respectively, and first and second inner layers formed from a plurality of inelastically stretchable non-elastomeric threads accumulated one upon another and stretchably extending in said waist-surrounding direction so as to describe curves between each pair of adjacent joining spots on inner sides of said first and second intermediate layers, respectively, wherein said first and second outer layers define said first and second surfaces, respectively.

2. The wearing article as recited by claim 1, wherein said first outer layer, said first intermediate layer and said first inner layer of said first composite sheet have a basis weight in a range of 5 to 25 g/m$^2$, respectively, while said second outer layer, said second intermediate layer and said second inner layer of said second composite sheet have a basis weight of at least 5 g/m$^2$.

3. The wearing article as recited by claim 1, wherein, outside a periphery of said sheet strip, the inelastic threads of said first inner layer and the inelastic threads of said second outer layer are intertangled together.

* * * * *

UNITED STATES PATENT AND TRADEMARK OFFICE
CERTIFICATE OF CORRECTION

PATENT NO. : 7,214,849 B2 Page 1 of 1
APPLICATION NO. : 11/074639
DATED : May 8, 2007
INVENTOR(S) : Satoru Sakaguchi et al.

It is certified that error appears in the above-identified patent and that said Letters Patent is hereby corrected as shown below:

Title page, Item (75) Inventors:

Please amend the first Inventor's name as follows from "Saturo SAKAGUCHI" to --Satoru Sakaguchi--.

Signed and Sealed this

Seventh Day of August, 2007

JON W. DUDAS
*Director of the United States Patent and Trademark Office*